United States Patent [19]

Leston

[11] 4,046,818

[45] Sept. 6, 1977

[54] PURIFICATION OF 3,5-DIALKYLPHENOLS

[75] Inventor: Gerd Leston, Pittsburgh, Pa.

[73] Assignee: Koppers Company, Inc., Pittsburgh, Pa.

[21] Appl. No.: 590,458

[22] Filed: June 26, 1975

[51] Int. Cl.$^2$ ............... C07C 37/22; C07C 39/06
[52] U.S. Cl. ............... 260/627 G; 260/624 A
[58] Field of Search ........... 260/512 R, 621 A, 621 B, 260/627 G, 624 A,

[56] References Cited

U.S. PATENT DOCUMENTS

| 2,327,312 | 8/1943 | Luten et al. | 260/621 A |
|---|---|---|---|
| 2,732,393 | 1/1956 | Hardy | 260/621 R |
| 3,159,685 | 12/1964 | Bradley et al. | 260/619 R |
| 3,401,205 | 9/1968 | Yoon | 260/623 R |

Primary Examiner—James O. Thomas, Jr.
Assistant Examiner—W. B. Lone
Attorney, Agent, or Firm—Kenneth J. Stachel; Herbert J. Zeh, Jr.; Oscar B. Brumback

[57] ABSTRACT

A 3,5-dialkylphenol having alkyl groups that are primary or secondary and that have a sum total of carbon atoms greater than two is separated from a mixture which also contains other dialkylphenols and monoalkylphenols. The mixture is subjected to a selective sulfonation in order that all the compounds in the mixture, except the 3,5-dialkylphenol, are sulfonated. Then, the unsulfonated 3,5-dialkylphenol and the sulfonated compounds are separated, and the purified 3,5-dialkylphenol is recovered.

9 Claims, No Drawings

PURIFICATION OF 3,5-DIALKYLPHENOLS

BACKGROUND OF THE INVENTION

This invention relates to a process for separating a 3,5-dialkylphenol wherein the alkyl groups are primary or secondary and have a sum total of carbon atoms greater than two from a mixture containing mono-alkylphenols and dialkylphenols other than 3,5-substituted. More particularly, this invention relates to a process for separating 5-isopropyl-m-cresol (m-thymol) from a mixture containing other isopropyl-cresols and possibly some di-isopropylphenols other than 3,5-dialkylphenols.

Some methods of producing a desired compound also involves the production of by-products or isomers. This is especially true in the production of 3,5-dialkylphenols where the alkyl groups are primary or secondary and have a sum total number of carbon atoms greater than two. Most methods for the production of these 3,5-dialkylphenols produce undesired isomers where the alkyl group is attached to the aromatic ring at a position other than the third and fifth positions. One example of such a 3,5-dialkylphenol is 3-isopropyl-5-methylphenol. Most of the methods available for producing this compound also produce undesirable isomers which include: 6-isopropyl-m-cresol; 2-isopropyl-m-cresol; 4-isopropyl-m- 3-isopropyl-p-cresol; 2,4-di-isopropylphenol; 2,5and possibly other di-isopropylphenols. -isopropyl-m-cresol; 4-isopropyl-m-cresol; 3-isopropyl-p-cresol, The compound 3-isopropyl-5-methylphenol is useful as an intermediate for preparing insecticides, e.g., its N-methyl carbamate derivative. In addition, the 3-isopropyl-5-methylphenol and other 3,5-dialkyphenols are valuable intermediates for preparing other compounds. It should be noted that 3-isopropyl-5-methylphenol is commonly referred to in the literature by several other names. In addition to 3-isopropyl-5-methylphenol, the compound has been referred to as 5-isopropyl-m-cresol, symmetrical thymol (sym-thymol), 5-thymol, or m-thymol. It was postulated at a symposium on "Carbamate Insecticides" at the 148th ACS meeting in the fall of 1964 that the order of insecticidial activity of alkylphenol-N-methyl carbamate was m-alkyl>o-alkyl or para-alkyl, sec-alkyl>tert-alkyl>n-alkyl and 4-carbon side chain>3 or 5carbon>fewer or more carbons. Therefore, the N-methyl carbamate of 5-isopropyl-m-cresol would be a very effective insecticide. In fact, the N-methyl carbamate of this compound has been patented for this use. See Jaeger and Teissker, German Pat. No. 1,147,438.

Alkylation of m-cresol with propylene or isomerization or transalkylation of other isopropyl-m-cresols produce a mixture of the isomers of 5-isopropyl-m-cresol and similar compounds. These compounds include mono- or poly-isopropyl-m-cresols as well as di-isopropylphenols and unalkylated cresols. When m-cresol is alkylated with propylene a mixture is obtained that contains 5-isopropyl-m-cresol and the following compounds: m-cresol, 6-isopropyl-m-cresol (thymol); 4-isopropyl-m-cresol (p-thymol); 2-isopropyl-p-cresol; 3-isopropyl-p-cresol and possibly 2,4-di-isopropylphenol and 2,5-di-isopropylphenol. Some of the compounds in this mixture have boiling points that are considerably different from the boiling point of 5-isopropyl-m-cresol. Therefore, these compounds can be easily removed from the mixture by fractional distillation. These compounds are 2-isopropyl-p-cresol, and 6-isopropyl-m-cresol. As can be seen from the boiling points listed in Table I below, complete separation of 5-isopropyl-m-cresol from the other compounds in the mixture having similar boiling points is extremely difficult.

Table I

|  | Boiling Points ° C at 760 mm Hg |
|---|---|
| Thymol (6-isopropyl-m-cresol) | 233 |
| 2-isopropyl-p-cresol | 228–233 |
| m-thymol (5-isopropyl-m-cresol) | 241 |
| p-thymol (4-isopropyl-m-cresol) | 245–246 |
| 3-isopropyl-p-cresol | 245 |
| 2,4-di-isopropylphenol | 248 |
| 2,5-di-isopropylphenol | 248[(1)] |

[(1)] 2,5-di-isopropylphenol has no normal b.p. given in the literature but it should boil around the same temperature as its 2,4 isomer, i.e., 248° C.

Compounds which boil at a lower temperature than m-thymol can be separated from the mixture and from m-thymol by fractional distillation. Also, these compounds can be separated readily from m-thymol by the process of this invention. Therefore, these compounds need not be removed from the mixture in order to separate m-thymol from the mixture. Of the compounds in Table I having a higher boiling point than m-thymol, p-thymol and 3-isopropyl-p-cresol have boiling points that are only slightly higher than the boiling point of m-thymol. These small differences are not enough to enable these compounds to be separated by distillation from the m-thymol. Regardless of the method of distillation, these compounds still will be present in any m-thymol boiling fraction of the mixture. By the process of the present invention m-thymol can be separated easily and efficiently from a mixture containing the compunds in Table I.

In the German Offenlegungsschrift No. 2,340,218, there is disclosed a method for recovering m-thymol from a mixture of isopropyl-cresols. This method involves akylating the mixture of isopropylcresols with an alkylating agent so that the 5-isopropyl-m-cresol is not alkylated. The 5-isopropyl-m-cresol is then separated from the mixture of alkylated-isopropyl-cresols by fractional distillation or by extraction when 2,6-di-isopropyl-p-cresol is present in the mixture of isopropyl-cresols. This selection alkylation and separation effectively purifies the 5-isopropyl-m-cresol from the mixture of alkylated-isopropyl-cresols. This method does not mention any possible use for the mixture of alkylated-isopropylcresols after m-thymol is separated from it. This mixture of alkylated-isopropylcresols would be best utilized if it could be isomerized to thymol or m-thymol. Before such an isomerization could take place in the above method, the alkylated-isopropylcresol mixture would have to be dealkylated. Such a dealkylation of this mixture would be difficult to perform because of the presence of the methyl group on the benzene ring. Any dealkylation of the alkylated isopropylcresols would probably remove both alkyl groups, the added alkyl group and the isopropyl group, from the benzene ring. Furthermore, isomerization of the methyl groups and transalkylation from one phenol nucleus to another would occur. Therefore, the production of any thymol or m-thymol by the isomerization of a mixture of alkylated-isopropylcresols would be troublesome.

Another method used in the art to separate compounds having similar boiling points is sulfonation. The art gives conflicting reports on whether or not compounds like m-thymol can be sulfonated. German Pat.

No. 283,306 by F. Raschig in 1914 showed that 3,5-xylenol, a compound similar to m-thymol, sulfonated by treating it with sulfuric acid. This sulfonation yields 1,3-dimethyl-5-hydroxy-4-sulfonic acid. In 1928 Horst Bruckner in Z. ANAL. CHEM. 75:289-92, while trying to separate meta-, and para-cresols and other phenols by sulfonation, determined that only one phenol, 3,5-xylenol would not sulfonate with concentrated sulfuric acid.

In U.S. Pat. No. 2,840,616, entitled "Production of Thymol", there is disclosed a method of converting thymol isomers to thymol. This method involves: Sulfonating thymol isomers, isomerizing the resulting sulfonic acid, desulfonating the product of the isomerization to produce a mixture of thymol and thymol isomers and recovering the thymol from the thymol isomers. A thymol isomer is defined as a compound having a general formula of m-cresol with an isopropyl radical located at one of the positions other than that ortho to the hydroxyl radical and para to the methyl radical in the benzene ring. The sulfonation of these thymol isomers is conducted with two or more moles of concentrated sulfuric acid or fuming sulfuric acid at a temperature near 100° C. This disclosure indicates that m-thymol is sulfonated with the other thymol isomers to produce the sulfonic acid of the thymol isomers.

SUMMARY OF THE INVENTION

In accordance with the present invention a method is provided for separating 3,5-dialkylphenols, wherein the alkyl groups are primary and/or secondary and have a sum total number of carbon atoms greater than two, from a mixture also containing mono-alkylphenols and other dialkylphenols. Instead of containing both mono-alkylphenols and other dialkylphenols, the mixture may contain only one or more mono-alkylphenols or one or more other dialkylphenols. The method is based on the discovery that in such a mixture the 3,5-dialkylphenol does not undergo sulfonation while the mono-alkylphenols and other dialkylphenols do undergo sulfonation.

Accordingly, the method in its broadest aspects comprises selectively sulfonating this mixture containing 3,5-dialkylphenol wherein the alkyl groups are primary and/or secondary and have a sum total number of carbon atoms greater than two, and one or more mono-alkylphenols and other dialkylphenols so that the 3,5-dialkylphenol is not sulfonated but the other compounds are sulfonated. Then, the unsulfonated 3,5-dialkylphenol is separated from the sulfonated compounds. The selective sulfonation proceeds by treating this mixture with at least one mole of a sulfonating agent per mole of mono-alkylphenols and other dialkylphenols in the mixture. This selective sulfonation produces the sulfonic acids of the mono-alkylphenols and other dialkylphenols. These sulfonic acids are water-soluble; and therefore, may be readily separated from the unsulfonated 3,5-dialkylphenol by water dilution. The water dilution may be performed in combination with the addition of an inert organic solvent to remove the unsulfonated 3,5-dialkylphenol. Distillation of the inert organic solvent permits recovery of the 3,5-dialkylphenol. The mono-alkylphenols and other dialkylphenols in the aqueous solution as sulfonic acids may be recovered by desulfonating the sulfonic acids during steam distillation. This allows the further use of the mono-alkylphenols and other dialkylphenols that remain in the mixture after separation.

The sulfonation is conducted in a conventional manner in the presence or absence of a solvent. If a solvent is used, it is preferably a paraffinic or naphthenic hydrocarbon. There are many well-known sulfonating agents, each having its own optimum sulfonation conditions. Preferred sulfonating agents are concentrated sulfuric acid, fuming sulfuric acid, and sulfur trioxide.

The mixture of mono-alkylphenols and other dialkylphenols may contain any quantity of 3,5-dialkylphenol. Preferably, the mixture contains a greater quantity of 3,5-dialkylphenol and a lesser quantity of mono-alkylphenols and other dialkylphenols. This mixture can be obtained in a known manner for the production of 3,5-dialkylphenol, for example, by alkylating cresol with a secondary alkyl or by isomerization of secondary alkyl cresol. The mixture can also be obtained as a by-product in the production of other secondary alkyl cresols, e.g., thymol.

The 3,5-dialkylphenols that can be purified by the process of this invention have the following formula:

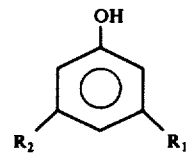

$R_1$ and $R_2$ are selected independently from the group consisting of primary or secondary alkyl groups and wherein the number of carbon atoms in both $R_1$ and $R_2$ when combined give a value greater than two. The term "mono-alkylphenol" means phenolic compounds that have only one R group, for example, cresol. This R group may be any alkyl group primary, secondary or tertiary having any number of carbon atoms. The term "other dialkylphenols" means phenolic compounds that have two R groups, which may be primary, secondary or tertiary with any number of carbon atoms, substituted on the aromatic ring at positions other than the three or five positions.

DETAILED DESCRIPTION OF THE INVENTION

The method of this invention is used to purify 3,5-dialkylphenols that have alkyl groups which are primary and/or secondary and have a sum total number of carbon atoms greater than two and preferably less than 10. This 3,5-dialkylphenol can be separated from a mixture containing the 3,5-dialkylphenol and other dialkylphenols and/or mono-alkylphenols.

The method of this invention is especially useful for separating this 3,5-dialkylphenol from mono-alkylphenols and/or other dialkylphenols that have a similar boiling point to the boiling point of the 3,5-dialkylphenol. Such a separation would be difficult by distillation. An example of such a separation is the separation of the 3,5-dialkylphenol, 3-isopropyl-5-methylphenol also known as 5-isopropyl-m-cresol, (hereinafter referred to as m-thymol) from 4-isopropyl-5-methylphenol or 3-isopropyl-4-methylphenol or 2,4-di-isopropylphenol or 2,5-di-isopropylphenol or any mixture of these compounds. The 3,5-dialkylphenol also may be separated from mono-alkylphenols and other dialkylphenols that have different boiling points than that of the 3,5-dialkylphenol.

The method of this invention is used preferably to purify m-thymol from a mixture containing the m-thymol and other isopropylcresols and diisopropylphenols other than 3,5-isopropylphenol with perhaps a small amount of mono-alkylphenols. Some of these compounds have boiling points that are similar to the boiling point of m-thymol and some have boiling points that are different from that of m-thymol. This mixture is produced from the preparation of m-thymol. This preparation may be by alkylating cresol with propylene or by isomerization of isopropylcresols or by any other method which produces m-thymol contaminated by other isopropylcresols and di-isopropylphenols other than 3,5-di-isopropylphenol. This mixture of m-thymol along with other isopropylcresols and di-isopropylphenols other than 3,5-di-isopropylphenol is composed mainly of the following compounds: m-thymol as the mahor constituent and p-thymol or 4-isopropyl-m-cresol; 3-isopropyl-p-cresol; 2,4-di-isopropylphenol; 2,5-di-isopropylphenol and possibly thymol, 6-isopropyl-m-cresol, and 2-isopropyl-p-cresol. The compounds in this mixture other than the m-thymol, which are present in lesser quantities, are hereinafter referred to as contaminants.

The mixture is subjected preferably to sulfonation with concentrated sulfuric acid at conventional conditions of temperature, pressure and residence time. These conventional conditions of sulfonation are usually a temperature in the range of room temperature to 150° C. preferably, 75° to 125° C., a pressure at atmospheric pressure and a residence time in the range of about one to three hours. The amount of concentrated sulfuric acid used to selectively sulfonate the mixture is at least one mole per mole of contaminants. Preferably, one to four moles of concentrated sulfuric acid is used per mole of contaminants. There must be at least one mole of concentrated sulfuric acid in order to sulfonate all the contaminants in the mixture. When sulfonating with one mole of concentrated sulfuric acid, the products of the reaction are one mole of sulfonic acid and one mole of water. Therefore, as the sulfonation progresses the sulfonating agent, i.e., concentrated sulfuric acid, becomes weaker. This weakening is caused by the dilution of the sulfonating agent with the water produced by the sulfonation reaction. In order to have a sulfonating agent of sufficient strength, the quantity of the sulfonating agent must be at least one mole per mole of compound to be sulfonated, i.e., contaminants of the mixture. The upper limit of four moles of sulfonating agent or concentrated sulfuric acid is set for economic reasons. Any quantity of sulfuric acid in excess of four moles per mole of contaminants may be used. Such a use would be an economic waste because the sulfonating agent left after selective sulfonation of the contaminants would still be a good sulfonating agent. The most economic operation of the selective sulfonation of the contaminants is that where none of the sulfonating agent or only a sulfonating agent that is too weak to sulfonate is remaining after sulfonation. Under the above conditions the contaminants in the mixture are selectively sulfonated while the m-thymol is not sulfonated.

It is believed, but the process of this invention is not limited by this belief, that the m-thymol is not sulfonated because of steric hindrance within the m-thymol molecule. The contaminants of the mixture are less sterically hindered and, therefore, form the sulfonic acids of the isopropylcresols and the isopropylphenols present in the mixture. The contaminants can sulfonate in the following manner: p-thymol is not sterically hindered in the six position and should sulfonate in the six position, 3-isopropyl-p-cresol should sulfonate in the six position, 2-isopropyl-p-cresol should sulfonate in the six position, and 2,5-di-isopropylphenol should sulfonate in the four position. Thymol should sulfonate in the four position.

Since the sulfonic acids of the contaminants are water soluble and the unsulfonated m-thymol is not water soluble, the sulfonic acids and the m-thymol may be easily separated. This separation is carried out by extraction. The sulfonic acids and unsulfonated m-thymol mixture is diluted preferably with water and extracted to leave the purified m-thymol. The separation may also be accomplished by mechanically separating the sulfonic acid layer from the m-thymol layer. Also, instead of extracting the sulfonic acid from the m-thymol by dilution with water the m-thymol may be extracted from the sulfonic acid by the addition of an organic solvent. These various separation methods yield a purified m-thymol and a mixture of sulfonic acids of the contaminants.

The mixture of sulfonic acids may be easily desulfonated. This desulfonation may occur in any manner known to those skilled in the art, such as heating with water to effect hydrolysis. This desulfonation would yield a mixture of isopropylcresols and di-isopropylphenols that could be subjected to isomerization by any method known to those skilled in the art to produce thymol or m-thymol from the isopropylcresols.

This process can readily be modified for continuous operation. This can be accomplished by providing several reaction vessels and cascading the reactants from one to the other with a predetermined holding time in each vessel.

For a better understanding of the invention, reference should be had to the following description of five experimental runs.

EXAMPLE 1

In this example an excess amount of sulfuric acid was used to sulfonate the contaminants in admixture with m-thymol. A 5.0 gram (33 mmol) sample of m-thymol, which contains about two percent (.66 mmol) of p-thymol and one percent (0.33 mmol) thymol was heated together with 1.0 gram (10 mmol) of concentrated sulfuric acid in a 50 mm flask for three hours on a steam bath with occasional shaking. The amount of sulfuric acid used is comparable to 10 moles of sulfuric acid per mole of contaminant. After this sulfonation, the mixture of sulfonic acids of the contaminants and the unsulfonated m-thymol was cooled to room temperature and diluted with 35 ml of water. Two layers separated. The top layer remained a liquid even on further cooling, but it solidified when seeded with a sample of 97 percent thymol. This solidified product was crushed, filtered, triturated with water and refiltered to give 4.0 grams of a yellow solid. This yellow solid melted at 49° C., which is the melting point of m-thymol, while the starting material had a melting point of 47° to 48° C.

Gas chromatographic analysis showed only m-thymol eluting at 21.1 minutes. Gas chromatographic analysis of the starting sample showed thymol eluting at 8.8 min. and m-thymol eluting at 12.1 min. and p-thymol eluting at 13.5 min. A small sample of the product was recrystalized from hexane without change in melting point or gas chromatographic analysis. A gas chromatographic analysis on an instrument equipped with a flame ionization detector showed small amounts of various impurities including p-thymol but the amount of these impurities was too small to be detected on a thermal conductivity cell.

EXAMPLE II

A sample of 90 percent pure m-thymol weighing 216.1 gm. (1.44 moles) and containing 0.4 moles of contaminants was introduced into a 500 ml flask with 43.2 gms. (.44 moles) of concentrated sulfuric acid. This amount of sulfuric acid corresponds to 3 moles per mole of contaminant. The materials were stirred and heated together to about 100° C. during 1 hour and held at this temperature for three more hours. Then the mixture was cooled and almost one liter of water was added. The solid that was obtained from this extraction was filtered, heated with water, stirred, cooled and refiltered. The product was dried under vacuum to a constant weight of 170.1 gm. which was 79 percent recovery. This product gave a melting point of 48° C. A sample of this product was analyzed by gas chromatography and the results showed that the m-thymol had a purity of 98.2% based on area %. This sample also contained 0.95% of p-thymol, 0.05% phenol and o-cresol, 0.44% m, p-cresol, 0.15% thymol and 2-isopropyl-m-cresol, 0.45% 2,4-di-isopropylphenol, 0.13% 5-ethyl-m-cresol and four unknowns totalling 0.41%.

The filtrate from the sulfonation was introduced intto a flask to concentrate it and to steam distill the phenols and hydrolyze the sulfonic acids of the contaminants in order to desulfonate the contaminants. The 800-900 ml of filtrate was distilled until excessive charring occurred and this produced two distillates. The first distillate boiled to 105° C. and amounted to about 500 ml. This distillate was extracted twice with 125 ml of ether. The ether extracts were dried with sodium sulfate and left a 3.6 gm. sample of yellow oil. This sample was analyzed by gas chromatography which showed that the purity of m-thymol was 85.2% with 11.5% of p-thymol. The second steam distillate boiled at 105° and 140°C. and amounted to about 200 ml. This second distillate was extracted with three 50 ml portions of ether. The extract was dried and evaporated and it yielded 4.8 gms. of solid. This solid was analysed by gas chromatography which showed the purity of m-thymol was 48% along with 20% of p-thymol based on area %. These two distillates could be recycled to the sulfonation step.

EXAMPLE III

A 20 gram (122 mmol) sample of impure 5-sec-butyl-m-cresol containing 2.8% (3.4 mmol) of low boiling compounds and 18.3% (22.3 mmol) of 4-sec-butyl-m-cresol was stirred with 8.0 gram (81.6 mmol) of concentrated sulfuric acid for 3.5 hours on a steam bath. The amount of sulfuric acid used is comparable to 3 moles of sulfuric acid per mole of contaminants. After this sulfonation, the product mixture was cooled and 50 ml of crushed ice was added. The layers were separated and the upper layer, which was the organic layer, was analyzed by gas chromatography. The chromatograph showed 8.0% low boiling compounds, 91.2% 5-sec-butyl-m-cresol and 0.8% of the 4sec-butyl-m-cresol. The increase in low boiling compounds is not of any great consequence since these compounds can be separated from the 5-sec-butyl-m-cresol by distillation.

EXAMPLE IV

A 20 gram (122 mmol) sample of impure 5-sec-butyl-m-cresol containing some low boilers and 18.6% (22.7 mmol) 4-sec-butyl-m-cresol was stirred with 8.0 gram (81.6 mmol) of concentrated sulfuric acid for 4.5 hours on a steam bath. The amount of sulfuric acid used is comparable to 3.5 moles of sulfuric acid to one mole of contaminants. At the completion of the sulfonation, the mixture was cooled and mixed with 50 ml of crushed ice. The layers were separated and the upper organic layer showed 1.1% low boiling compounds (2 peaks) and 3.5% 4-sec-butyl-m-cresol by gas chromatographic analysis.

EXAMPLE V

A 19.2 gram (107.9 mmol) charge of 5-cyclohexyl-m-cresol containing 12.0% (13 mmol) low boiling compounds and 17.9% (19.3 mmol) 6-cyclohexyl-m-cresol was reacted for 4.0 hours with 9.0 grams (91.8 mmol) of concentrated sulfuric acid on a steam bath. The amount of sulfuric acid used is comparable to about 2.8 moles of sulfuric acid per mole of contaminants. After sulfonation, the product mixture was cooled and diluted with 50 ml of crushed ice. The organic material was extracted with benzene and the benzene layer was analyzed by gas chromatography which showed 4.6% lower boiling compounds and 6.9% 6-cyclohexyl-m-cresol.

According to the provisions of the patent statutes, the principle, preferred construction and mode of operation of the invention have been explained and what is considered to represent its best embodiment has been illustrated and described. However, it should be understood that within the scope of the appended claims, the invention may be practiced otherwise than as specifically illustrated and described.

I claim:

1. A method of purifying 3,5-dialkylphenols from a mixture containing monoalkylphenols and other dialkylphenols wherein the 3,5-dialkylphenol has alkyl groups which are primary or secondary and have a sum total number of carbon atoms greater than 2, comprising:
    a. subjecting said mixture to sulfonation with a sulfonating agent selected from the group consisting of sulfuric acid, fuming sulfuric acid, or sulfur trioxide in an amount of at least one mole of sulfonating agent per mole of compound other than 3,5-dialkylphenol present in said mixture and at a temperature in the range of room temperature to 150° C at atmospheric pressure whereby all the compounds in said mixture other than said 3,5-dialkylphenol are converted to sulfonic acids, and
    b. separating said sulfonic acids from the unsulfonated 3,5-dialkylphenol to produce a purified 3,5-dialkylphenol.

2. A method according to claim 1 in which the separation is performed by extraction with water.

3. A method according to claim 2 in which the sulfonation is conducted in an inert organic solvent.

4. A method of purifying 5-isopropyl-m-cresol from a mixture of 5-isopropyl-m-cresol and 4-isopropyl-m-cresol comprising:
    a. subjecting said mixture to sulfonation with a sulfonating agent selected from the group consisting of sulfuric acid, fuming sulfuric acid, or sulfur trioxide in an amount of at least one mole of sulfonating agent per mole of 4-isopropyl-m-cresol and at a temperature in the range of room temperature to 150° C at atmospheric pressure whereby the 4-isopropyl-m-cresol is sulfonated to form a sulfonic acid and the 5-isopropyl-m-cresol remains unsulfonated, and;

b. separating the sulfonic acid of 4-isopropyl-m-cresol in said mixture from the unsulfonated 5-isopropyl-m-cresol in said mixture to produce a purified 5-isopropyl-m-cresol.

5. A method according to claim 4 wherein said mixture of 5-isopropyl-m-cresol and 4-isopropyl-m-cresol also contains 3-isopropyl-p-cresol, 2,4-di-isopropylphenol and 2,5-di-isopropylphenol which form sulfonic acids along with 4-isopropyl-m-cresol when the mixture is subjected to sulfonation with at least one mole of a sulfonating agent selected from the group consisting of sulfuric acid, fuming sulfuric acid, or sulfur trioxide per mole of 4-isopropyl-m-cresol, 3-isopropyl-p-cresol, 2,4di-isopropylphenol and 2,5-di-isopropylphenol and are separated from 5-isopropyl-m-cresol.

6. A method according to claim 5 wherein 5-isopropyl-m-cresol is the major constituent of the mixture.

7. A method according to claim 6 wherein said mixture also includes 2-isopropyl-p-cresol and 6-isopropyl-m-cresol.

8. A method according to claim 6 wherein the separation of sulfonic acids from unsulfonated 5-isopropyl-m-cresol is performed by mechanical separation.

9. A method according to claim 6 wherein the separation of sulfonic acids from unsulfonated 5-isopropyl-m-cresol is performed by extraction with water.

* * * * *